(12) United States Patent
Bosteels

(10) Patent No.: US 10,418,922 B1
(45) Date of Patent: Sep. 17, 2019

(54) CALIBRATION OF 3-PHASE MOTOR CURRENT SENSING FOR SURGICAL ROBOTIC ACTUATORS

(71) Applicant: Verb Surgical Inc., Mountain View, CA (US)

(72) Inventor: Jan Bosteels, San Jose, CA (US)

(73) Assignee: Verb Surgical Inc., Mountain View, CA (US)

( * ) Notice: Subject to any disclaimer, the term of this patent is extended or adjusted under 35 U.S.C. 154(b) by 0 days.

(21) Appl. No.: 16/010,291

(22) Filed: Jun. 15, 2018

(51) Int. Cl.
| | |
|---|---|
| H02P 6/10 | (2006.01) |
| H02P 6/12 | (2006.01) |
| G01R 35/00 | (2006.01) |
| G01R 31/34 | (2006.01) |
| A61B 34/37 | (2016.01) |

(52) U.S. Cl.
CPC .............. *H02P 6/10* (2013.01); *A61B 34/37* (2016.02); *G01R 31/343* (2013.01); *G01R 35/005* (2013.01); *H02P 6/12* (2013.01)

(58) Field of Classification Search
CPC ...................................................... H02P 6/10
USPC ............................... 318/400.23, 400.01, 700
See application file for complete search history.

(56) References Cited

U.S. PATENT DOCUMENTS

| | | |
|---|---|---|
| 6,452,405 B1 | 9/2002 | Collier-Hallman |
| 8,004,141 B2 | 8/2011 | Jeung |
| 8,853,979 B2 * | 10/2014 | Wu ........................... H02P 6/20 |
| | | 318/400.02 |
| 2006/0001392 A1 | 1/2006 | Ajima et al. |
| 2008/0100243 A1 | 5/2008 | Kurosawa et al. |

FOREIGN PATENT DOCUMENTS

WO  2010/045965 A1  4/2010

OTHER PUBLICATIONS

International Search Report and Written Opinion dated Feb. 28, 2019 for related PCT Application No. PCT/US2018/038045 6 Pages.
Libor Prokop, et al., Control with Sensorless Back EMF Zero Crossing Detection Using 56F80X, Freescale Semiconductor Application Note, pp. 1-56, Nov. 2005.
3-Phase BLDC Drive Using Variable DC Link Six-Step Inverter, Design Reference Manual, Freescale Semicondutor, pp. 1-52, May 2006.

* cited by examiner

*Primary Examiner* — David Luo
(74) *Attorney, Agent, or Firm* — Womble Bond Dickinson (US) LLP

(57) ABSTRACT

A 3-phase motor driver circuit has a first input to be coupled to an output of a first phase current sensor, and a second input that represents a zero reference. A controller adjusts one or more of a first phase voltage, a second phase voltage, and a third phase voltage, until a comparison between the first input and the input indicates that the first input has reached the zero reference, and in response the controller captures an output of a second phase current sensor and an output of a third phase current sensor. The controller then stores, in memory, calibration data that is based on the captured outputs of the second and third phase current sensors. Other aspects are also described.

20 Claims, 3 Drawing Sheets

CALIBRATION OF 3-PHASE MOTOR CURRENT SENSING FOR SURGICAL ROBOTIC ACTUATORS

FIELD

An aspect of the disclosure here relates generally to electric motor phase current sensing and more particularly to calibration and self-test of phase current sensing for a brushless dc 3-phase Y-wired motor of a surgical robotic actuator. Other aspects are also described.

BACKGROUND

Distortion in the phase currents of an electric motor can contribute to motor torque ripple, which leads to rough actuator motion, especially at low speeds. This effect is observable in surgical robot arms that have multiple joints (each joint being actuated by one or more electric motors that may be running simultaneously), particularly when a user moves the arm by hand. The user feels the irregular actuation of the joints. Also, higher layer robot control algorithms that rely on operating a joint in torque mode (using the sensed phase current as feedback to compute a motor torque input command) are adversely impacted by the torque ripple. There is therefore a need for a calibration procedure that enables more accurate sensing of motor phase current which enables smoother control of a surgical robotic arm joint, by reducing the motor torque ripple. In addition, a power on self-test procedure is needed that verifies the integrity of the phase current sensing process.

SUMMARY

A method for calibration of 3-phase motor current sensing that may be used during a power on self-test of a motor driver circuit in a surgical robotic arm, is as follows. An output of a first phase current sensor is monitored while adjusting one or more of a first phase voltage, a second phase voltage, and a third phase voltage, until the monitored output reaches a zero reference. While the monitored output of the first phase current sensor is at the zero reference, an output of a second phase current sensor and an output of a third phase current sensor are captured. Calibration data that is based on the captured outputs of the second and third phase current sensors are then stored in memory. The method may be repeated to obtain, and store in the memory, further calibration data that is based on the captured outputs of the first and third phase current sensors, and still further calibration data that is based on the captured outputs of the first and second phase current sensors. The stored calibration data is then applied, during a normal mode of operation or "run time", to adjust the outputs of the current sensor, for improved accuracy of current sensing. The method may also be performed as part of each power on self-test, POST, procedure of a motor driver circuit, where the newly computed calibration data of each instance of POST is compared to previously computed and stored calibration data, and if the new calibration data does not deviate from the previous calibration data, then current sensing integrity may be deemed verified. After completion of the method, a calibration controller will adjust or compensate the output of each phase current sensor in accordance with the verified and stored calibration data, thereby yielding accurate, per-phase current measurements (despite manufacturing variations in the phase current sensors.)

The above described method is particularly effective when the three phase power stage has the following constraint: a separate pair of switches are coupled to each phase (of a first phase, a second phase, and a third phase) to develop the first phase voltage, the second phase voltage, and the third phase voltage, respectively, which induces a current in each phase that is monitored through outputs of the first, second and third phase current sensors, respectively; and wherein while monitoring the output of the first phase current sensor and capturing the outputs of the second and third phase current sensors, the separate pairs of switches that are coupled to the three phases are not operated to be both open at the same time. In other words, control of the three phase power stage is constrained even during the calibration mode of operation, in that the high side switch and the low side switch that are coupled to each phase are complementary, in that they cannot be operated to be both open at the same time.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Figure 1:
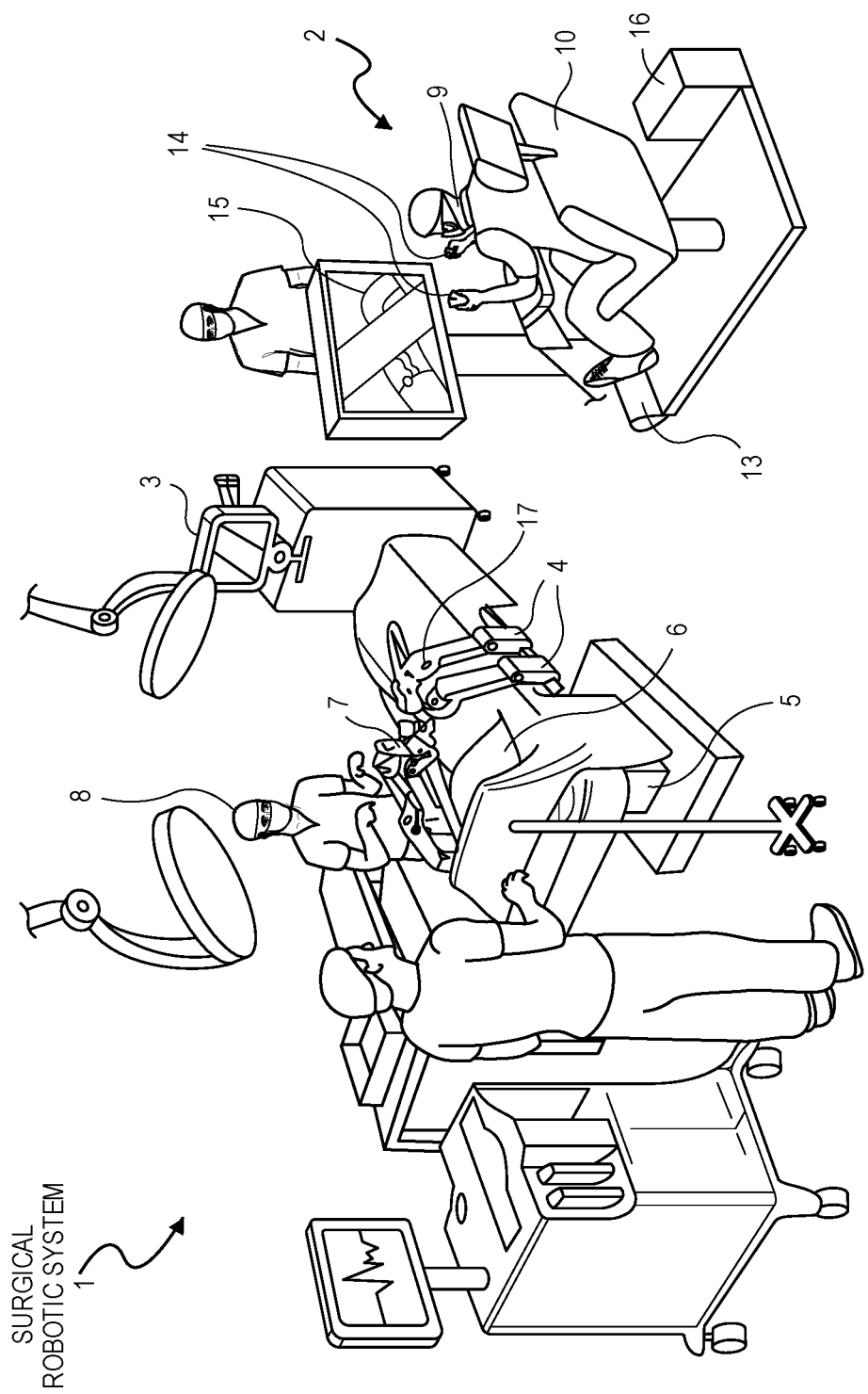
FIG. 1 is a pictorial view of an example surgical robotic system in an operating arena.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
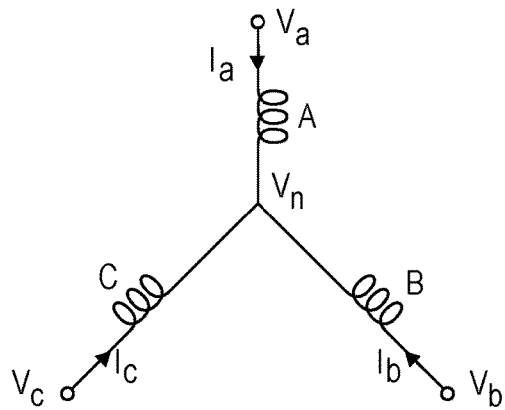
FIG. 2 is a diagram of an example 3-phase motor.
Figure 3:
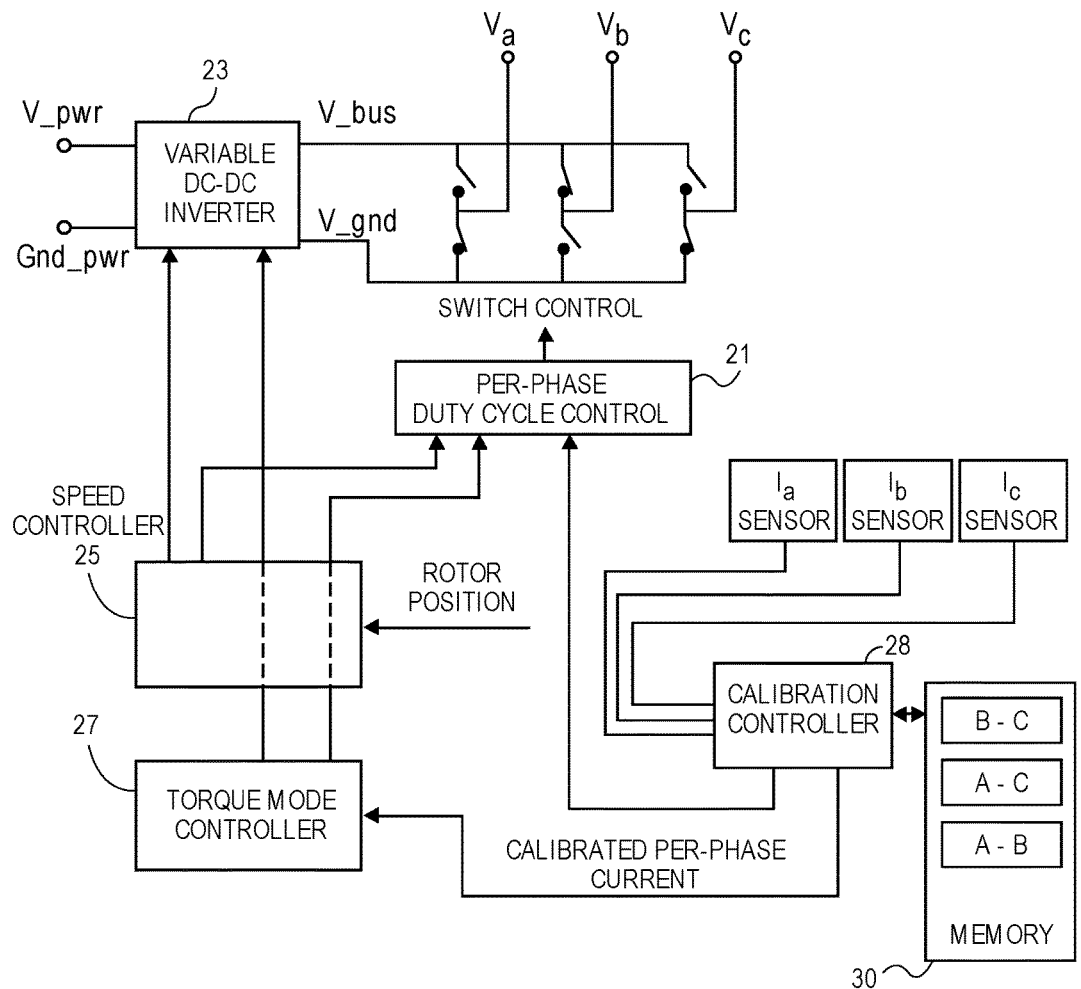
FIG. 3 is a block diagram of part of a 3-phase motor driver circuit.

FIG. 2 is a diagram of the windings of an example 3-phase motor that can be used to actuate a joint of a surgical robotic arm. FIG. 3 is a block diagram of part of a 3-phase motor driver circuit. The motor phases A, B, C (windings) in this example are Y-connected at a common node having voltage Vn. Each phase has a respective node (motor terminal) that develops a respective voltage Va, Vb, Vc, when the three phases are driven by the power stages of a voltage source inverter shown in FIG. 3 and which induces phase currents Ia, Ib, Ic as shown in FIG. 2. The power stage for each phase has a separate pair of switches, e.g., a high side switch coupled to V_bus and a low side switch coupled to V_gnd, whose common or shared node is coupled to their respective phase (motor terminal.) These switches, which may be MOSFETs or other suitable solid state devices that can operate as switches, serve to apply V_bus to each phase, under switch mode, variable duty-cycle control (e.g., variable turn on vs. turn off intervals of a constant frequency square wave) dictated by a per-phase duty cycle control logic circuit 21. V_bus may be produced by a variable dc-dc inverter 23 or by a fixed dc voltage regulator (not shown.) The resulting phase voltage Va, phase voltage Vb, and phase voltage Vc induce currents in the three phases (Ia, Ib, Ic) that are monitored through outputs of the current sensors Ia sensor, Ib sensor and Ic current sensor, respectively. Each current sensor may have or may operate based on i) a Hall effect sensor, ii) a current sense resistor that is coupled in series with the respective phase inductor, iii) a current mirror circuit that is coupled in series with the respective phase inductor, iv) a circuit that detects voltage across the on-resistance of a high side switch or a low side switch, or v) other circuits or arrangements that are suitable for sensing motor phase current. Further aspects of the current sensing will be described below.

The motor driver circuit in FIG. 3 may be suitable for controlling a brushless dc motor (e.g., a Y-connected, 3-phase motor as in FIG. 2), and may have a speed controller 25. The latter is an electronic circuit that obtains position feedback on the rotor of the motor, and on that basis controls the speed of the rotor in accordance with any suitable motor speed control algorithm. This algorithm may signal a desired V_bus and a desired per-phase duty cycle (to the per-phase duty cycle control logic 21.) A commutation handler (not shown) may be part of the duty cycle control logic 21 and is responsible for appropriate timing of the switch control pulses that operate the switches of each of the motor phases to ensure smooth motion of the rotor during regular or normal operation of the motor driver circuit. In addition, there may be a torque mode controller 27 (e.g., as part of a higher layer of abstraction than the speed controller 25) that may be used to limit the torque of the motor or maintain a constant torque output. That aspect in particular can benefit from calibrated, per-phase current measurements which are used to compute the current torque output.

The calibrated per-phase current measurements are provided by a calibration controller 28. The calibration controller 28 is configured, e.g., as a programmed digital processor, to operate the switches of the inverter during a calibration mode of operation. By appropriately controlling the switches, the calibration controller varies one or more of the phase voltages (the voltages on the external motor terminals that are directly connected to the phase inductors or windings of the motor), until a comparator (in the calibration controller) indicates that its first input (coming from a given phase current sensor) has reached a zero reference. The comparator (which may be implemented as an analog circuit or it may be implemented as part of the programmed digital processor) has its first input coupled to an output of a given phase current sensor (e.g., Ia sensor), and its second input represents the zero reference; there may be a separate instance of the comparator for each phase. The comparator serves to compare the signal at its first input to the zero reference, and may assert its output once the signal at its first input crosses into the zero reference. The zero reference may be a predetermined value range that represents zero phase current. The range may be determined using knowledge of the sensitivity of the current sensor circuitry (including any analog to digital conversion aspects to such circuitry, if applicable.) In response to the comparator indicating that its first input is at the zero reference, the calibration controller 28 captures the outputs of the other phase current sensors (here, Ib sensor and Ic sensor), and then stores, in memory 30, calibration data that is based on those captured outputs. This may be repeated to obtain three sets of calibration data which are stored in the memory 30, e.g., B-C data representing the captured outputs of the Ib sensor and the Ic sensor, A-C data for the captured outputs of the Ia and Ic sensors, and A-B data for the captured outputs of the Ia and Ib sensors. The calibration data in each set may be, for example, a ratio of the two captured outputs. Such calibration data is then used during the normal mode of operation, or "run time", to adjust or compensate the outputs of the current sensors so as to improve accuracy of the phase current sensing.

The following process and accompanying explanation (using circuit network theory and the example 3-phase circuit diagram in FIG. 2) shows how to obtain the per-phase calibration data. The per phase voltages Va, Vb and Vc may be controlled by the voltage source inverter (through signaling the per-phase duty cycle control logic 21—see FIG. 3), somewhere in the range of zero to V_bus, by adjusting the duty cycle for each phase. With the Y-connected arrangement shown, and the per-phase equivalent resistance being Ra, Rb, Rc, respectively, the current in each phase may be given by $$Ia=(Va-Vn)/Ra$$

$$Ib=(Vb-Vn)/Rb$$

$$Ic=(Vc-Vn)/Rc$$

Also, the sum of these currents is zero through Kirchoff's Law, Ia+Ib+Ic=0.

Now, the process may begin with establishing a zero offset value for each phase current sensor Ia, Ib, Ic, by turning off the voltage source inverter (signaling the variable dc-dc inverter 23 to turn its output off), and recording the output value of each current sensor as a "zero offset" value for that sensor. This error in the sensor output can thus be compensated or removed, by adding the recorded zero offset value to the actual sensor output value during normal operation mode.

In addition to the error that it exhibits when there is zero current (zero output error or offset), each current sensor also exhibits a so-called gain error, when its output is not zero. The gain error could depend on the inherent manufacturing variation or inaccuracy or imperfections of the sensor itself (which may encompass a sensor amplifier.) To find the gain error for each sensor, the process may begin with forcing zero current in a single phase, e.g., phase C. That means Vn=Vc, such that in the equations above, (Va−Vc)/Ra+(Vb−Vc)/Rb=0. Now, if we assume that Va=V+d and Vb=V−d, then there is a $$Vc=((V+d)Ra+(V-d)/Rb)/(1/Ra+1/Rb)$$

that will result in Ic=0 and Ia+Ib=0 where Ia=−Ib. A switch control algorithm can be readily written (implemented by the calibration controller 28) using knowledge of the 3-phase configuration and the inverter switches in FIG. 3 for example, that uses Ic as input and Vc as output, and that can find the Vc that gives Ic=0. The latter constraint, Ic=0, involves making a comparison between the output of the Ic sensor and a zero reference, as part of such an algorithm.

In one aspect, the algorithm determines what the duty cycle of the switches that are coupled to phase C should be, that results in Ic=0 (where this condition may be verified by the comparator in the calibration controller.) Note that it is also possible to configure the algorithm to "solve for" the duty cycles of the switches that are coupled to the other phases, here phase A and phase B. Thus, described more generally, the calibration controller 28 (including its comparison function) serve to monitor the output of a first phase current sensor while adjusting one or more of the first phase voltage, the second phase voltage, and the third phase voltage, until the monitored output reaches a zero reference. At that point (while the monitored output of the first phase current sensor is at the zero reference), the output of the second phase current sensor and the output of the third phase current sensor are captured by the calibration controller 28, and then stored in the memory 30. For example, when Ic=0, it is necessary that Ia=−Ib. As a result, the outputs of Ia sensor and Ib sensor should be equal and opposite. But the actual measurements will not be, and hence a measurement ratio may be established in order to equalize the actual measurement. More broadly, the outputs of the Ia sensor and Ib sensor are captured, and calibration data representing those outputs are stored in the memory 30 (depicted in FIG. 3 as A-B calibration data). The process may then be repeated for Ib=0 to yield A-C calibration data, and for Ia=0 to yield B-C calibration data.

In one aspect, each instance of the calibration data may include a ratio of the two captured outputs. Thus, the A-B data may be the ratio of the captured outputs of Ia sensor and Ib sensor. This ratio may then be multiplied by the output of Ib sensor during run-time, to correct for the gain error in the output of the Ib sensor relative to the Ia sensor. Similarly, the A-C data may be applied during run-time to the output of Ic sensor, to correct for the gain error in the output of the Ic sensor relative to the Ia sensor. And finally, the B-C data may be applied during run-time to the output of Ib sensor.

Note that the zero offset values described earlier may also be applied during run-time to as corrections to their respective current sensor outputs or readings, to further improve accuracy of the current sensing.

Figure 4:
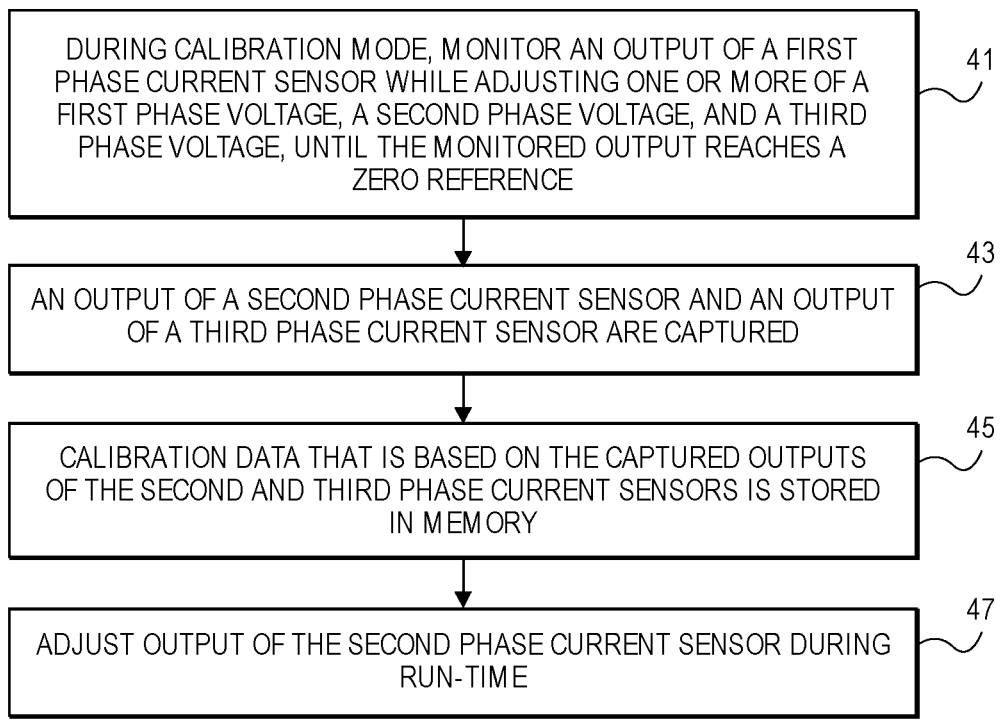
FIG. 4 is a flow diagram for an example method for calibration of 3-phase motor current sensing.

FIG. 4 is a flow diagram for an example method for calibration of 3-phase motor current sensing. The method may be performed by the calibration controller 28 of FIG. 3, for example entirely as digital signal processing operations performed by a programmed digital processor of a motor driver circuit, in a surgical robotic arm. The method includes monitoring an output of a first phase current sensor while adjusting one or more of a first phase voltage, a second phase voltage, and a third phase voltage, until the monitored output reaches a zero reference (operation 41.) While the monitored output of the first phase current sensor is at the zero reference, an output of a second phase current sensor and an output of a third phase current sensor are captured (operation 43). In one aspect, while monitoring the output of the first phase current sensor and capturing the outputs of the second and third phase current sensors, the separate pair of switches that are coupled to the first phase are not operated to be both open at the same time. The latter may be deemed to be a hardware constraint that has been placed on the per-phase duty cycle control logic 21, with respect to all of the phases (see FIG. 3.) Next, calibration data that is based on the captured outputs of the second and third phase current sensors is stored in memory (operation 45.)

The operations 41-45 may be performed during power on self test, POST, during which there may be an additional operation of comparing the newly determined calibration data to previously determined calibration data (and where the integrity of the previously determined and stored calibration data can be verified.) The POST may be performed each time the motor driver circuit is powered up.

After completion of the operations 41-45, e.g., as part of POST, the output of the second phase current sensor is adjusted during run-time or a normal mode of operation, in accordance with the newly computed and stored calibration data (operation 47.) In one aspect, the calibration data includes a ratio of the captured outputs of the second and third phase current sensors, and the output of the second phase current sensor may then be adjusted by for example multiplying the output of the second phase current sensor by the ratio.

Note that in the case of a 3-phase winding arrangement as depicted in FIG. 2, the operations 41, 43 (in which the one or more of the first phase voltage, the second phase voltage, and the third phase voltage are being adjusted) could be performed as follows: while monitoring the output of the first phase current sensor and capturing the outputs of the second and third phase current sensors, the pair of switches that are coupled to the first phase (and perhaps the pair of switches that are coupled to the second phase and to the third phase) are signaled to turn and off according to a duty cycle that induces equal and opposite currents in the second and third phases. In other words, since the condition to be met is that the current in the first phase be zero, the nature of the 3-phase Y-connected winding will require that the currents in the second and third phases be equal and opposite (when the output of the first phase current sensor is at the zero reference.)

While certain aspects have been described and shown in the accompanying drawings, it is to be understood that such are merely illustrative of and not restrictive on the broader disclosure, and that the disclosure is not limited to the specific constructions and arrangements shown and described, since various other modifications may occur to those of ordinary skill in the art. For example, while FIG. 2 depicts a voltage source inverter in which a single V_bus is applied to each phase, it is also possible to have different V_bus levels applied to different phases. The description is thus to be regarded as illustrative instead of limiting.

What is claimed is:

1. A method for calibration of 3-phase motor current sensing, comprising:
    monitoring an output of a first phase current sensor while adjusting one or more of a first phase voltage, a second phase voltage, and a third phase voltage, until the monitored output reaches a zero reference;
    capturing an output of a second phase current sensor and an output of a third phase current sensor while the monitored output of the first phase current sensor is at the zero reference; and storing in memory calibration data that is based on the captured outputs of the second and third phase current sensors.

2. The method of claim 1 performed during power on self test, POST.

3. The method of claim 2 further comprising
after completion of the POST, adjusting the output of the second phase current sensor in accordance with the stored calibration data.

4. The method of claim 3 wherein the calibration data comprises a ratio of the captured outputs of the second and third phase current sensors.

5. The method of claim 1 wherein adjusting the one or more of the first phase voltage, the second phase voltage, and the third phase voltage comprises
controlling a separate pair of switches that are coupled to each phase of a first phase, a second phase, and a third phase, which induces a current in each phase,
wherein while monitoring the output of the first phase current sensor and capturing the outputs of the second and third phase current sensors, the separate pair of switches that are coupled to each phase are not operated to be both open at the same time.

6. The method of claim 5 wherein the first phase, the second phase and the third phase are Y-connected.

7. The method of claim 1 wherein adjusting the one or more of the first phase voltage, the second phase voltage, and the third phase voltage comprises
controlling a separate pair of switches that are coupled to each phase of a first phase, a second phase, and a third phase, which induces a current in each phase,
wherein while monitoring the output of the first phase current sensor and capturing the outputs of the second and third phase current sensors, the separate pair of switches that are coupled to the first phase are signaled to turn and off according to a duty cycle that induces equal and opposite currents in the second and third phases.

8. The method of claim 1 further comprising:
a) monitoring the output of the second phase current sensor, while adjusting one of the first phase voltage, the second phase voltage, or the third phase voltage until the monitored output of the second phase current sensor reaches the zero reference;
b) capturing the output of the first phase current sensor and the output of the third phase current sensor while the monitored output of the second phase current sensor is at the zero reference; and
c) storing in memory further calibration data that is based on the captured outputs of the first and third phase current sensors in b).

9. The method of claim 8 wherein the further calibration data comprises a ratio of the captured outputs of the first and third phase current sensors in c), the method further comprising
adjusting the output of the second phase current sensor in accordance with the stored further calibration data.

10. The method of claim 8 further comprising
controlling a separate pair of switches that are coupled to each phase of a first phase, a second phase, and a third phase,
wherein while monitoring the output of the second phase current sensor and capturing the outputs of the first and third phase current sensors, the separate pair of switches that are coupled to each phase are not operated to be both open at the same time.

11. A 3-phase motor driver circuit comprising:
a controller configured to compare a first input from an output of a first phase current sensor with a second input that represents a zero reference, and adjust one or more of a first phase voltage, a second phase voltage, and a third phase voltage, until the comparison indicates that the first input has reached the zero reference, and in response to the comparison indicating that the first input is at the zero reference the controller captures an output of a second phase current sensor and an output of a third phase current sensor, wherein the controller is to then store, in memory, calibration data that is based on the captured outputs of the second and third phase current sensors.

12. The circuit of claim 11 wherein the controller is configured to compare the first input with the second input, adjust one or more of the phase voltages, and capture the output of the second phase current sensor and the the output of the third phase current sensor during power on self test, POST.

13. The circuit of claim 12 wherein the controller is configured to
after completion of the POST, adjust the output of the second phase current sensor in accordance with the stored calibration data.

14. The circuit of claim 13 wherein the calibration data comprises a ratio of the captured outputs of the second and third phase current sensors.

15. The circuit of claim 11 wherein the controller is configured to adjust the one or more of the first phase voltage, the second phase voltage, and the third phase voltage by
controlling a separate pair of switches that are coupled to each phase of a first phase, a second phase, and a third phase, which induces a current in each phase,
wherein while monitoring the output of the first phase current sensor and capturing the outputs of the second and third phase current sensors, the separate pair of switches that are coupled to each phase are not operated to be both open at the same time.

16. The circuit of claim 15 wherein the first phase, the second phase and the third phase are Y-connected.

17. The circuit of claim 11 wherein the controller is configured to adjust the one or more of the first phase voltage, the second phase voltage, and the third phase voltage by
controlling a separate pair of switches that are coupled to each phase of a first phase, a second phase, and a third phase, which induces a current in each phase,
wherein while monitoring the output of the first phase current sensor and capturing the outputs of the second and third phase current sensors, the separate pair of switches that are coupled to the first phase are signaled to turn and off according to a duty cycle that induces equal and opposite currents in the second and third phases.

18. The circuit of claim 11 wherein the controller is further configured to:
a) monitor the output of the second phase current sensor, while adjusting one of the first phase voltage, the second phase voltage, or the third phase voltage until the monitored output of the second phase current sensor reaches the zero reference;
b) capture the output of the first phase current sensor and the output of the third phase current sensor while the monitored output of the second phase current sensor is at the zero reference; and c) store in memory further calibration data that is based on the captured outputs of the first and third phase current sensors in b).

19. The circuit of claim 18 wherein the further calibration data comprises a ratio of the captured outputs of the first and third phase current sensors in c), the controller further configured to
  adjust the output of the second phase current sensor in accordance with the stored further calibration data.

20. The circuit of claim 18 wherein the controller is further configured to
  operate a separate pair of switches that are coupled to each phase of a first phase, a second phase, and a third phase,
  wherein while monitoring the output of the second phase current sensor and capturing the outputs of the first and third phase current sensors, the separate pair of switches that are coupled to each phase are not operated to be both open at the same time.

\* \* \* \* \*